United States Patent [19]

Waddan et al.

[11] 4,390,738

[45] Jun. 28, 1983

[54] PROCESS FOR THE OXIDATION OF OLEFINIC COMPOUNDS TO OLEFINE OXIDES OR DERIVATIVES THEREOF

[75] Inventors: Dhafir Y. Waddan, Whalley Range; Derek Williams, Middlesbrough, both of England

[73] Assignee: Imperial Chemical Industries PLC, London, England

[21] Appl. No.: 274,797

[22] Filed: Jun. 18, 1981

[30] Foreign Application Priority Data

Jun. 26, 1980 [GB] United Kingdom ................ 8020976

[51] Int. Cl.$^3$ ...................... C07C 31/20; C07C 33/04; C07D 301/06; C07D 301/08
[52] U.S. Cl. .................................... 568/857; 549/523; 549/533; 568/860; 568/867

[58] Field of Search ................. 568/857, 867; 260/348.33, 348.22; 560/860, 857; 549/533, 523

[56] References Cited

U.S. PATENT DOCUMENTS 2,649,463  8/1953  Skelly .............................. 260/348.33
4,008,286  2/1977  Hirose et al. ........................ 568/860

FOREIGN PATENT DOCUMENTS 1138361  1/1969  United Kingdom ........... 260/348.33

Primary Examiner—Joseph E. Evans
Attorney, Agent, or Firm—Cushman, Darby & Cushman

[57] ABSTRACT

Olefine oxides or derivatives thereof such as glycols are produced by reacting an olefinic compound e.g. ethylene, propylene or butadiene with oxygen in the presence of a catalyst containing copper bonded to a peroxo group.

9 Claims, No Drawings

PROCESS FOR THE OXIDATION OF OLEFINIC COMPOUNDS TO OLEFINE OXIDES OR DERIVATIVES THEREOF

The present invention relates to the oxidation of olefinic compounds to olefine oxides or to derivatives of olefine oxides.

According to the invention a process for the oxidation of olefinic compounds to olefinic oxides or derivatives thereof comprises reacting a compound containing an olefinic double bond with oxygen in the presence of a copper catalyst characterised in that the catalyst contains copper atoms to each one of which is bonded one or more peroxo groups.

The peroxo group bonded to a copper atom is represented by Cu-OO-X and the residual valency indicated by X may be satisfied by hydrogen and/or by bonding to another copper atom. The copper atoms which are bonded to the peroxo groups may form part of a complex structure which is insoluble in common solvents such as tetrahydrofuran and propionitrile and such complex structures are very suitable therefore as heterogeneous catalysts for liquid or gas phase reactions.

The catalysts may be prepared by the reaction of hydrogen peroxide with cuprous compounds or with cupric compounds, e.g. cupric acetate, which are readily converted to the cuprous form. A typical preparation using hydrogen peroxide is described in Inorg. Nucl. Chem. Letters Vol. 9 pp 987–990 1973 in which hydrogen peroxide is added to an aqueous solution of copper acetate to give an insoluble brown precipitate to which the authors tentatively gave the structure

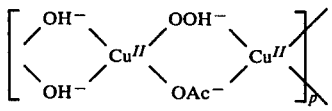

the peroxo group OOH$^-$ bridging copper atoms in the complex. We have found that the compound formed by the process described in the article in Inorg. Nucl. Chem. Letters is a catalyst, although not the best catalyst, for the process of our invention.

More effective catalysts may be prepared by the action of hydrogen peroxide on cuprous halides, particularly the bromide or chloride, or cuprous cyanide (solubilised in water by the presence of potassium cyanide or potassium hydroxide). As described in the article in Inorg. Nucl. Chem. Letters and in the Examples described later in this specification such preparations are preferably carried out in wholly or partially aqueous solution under mild preferably ambient temperature conditions. Water is the most convenient solvent for use for this reaction but if the copper compound is not sufficiently soluble in water than other solvents e.g. nitriles such as propionitrile, alcohols, e.g. $C_1$ to $C_6$ alkanols, ethers e.g. diglyme and other solvents listed later in this specification as being suitable for the oxidation process according to the invention may be used. The product precipitates from the solution and is ready for use after being suitably washed.

A further method of preparation of the catalysts is by the action of oxygen on certain copper compounds whereby a peroxo link is formed. For example, in an article in Chimia 1978 32(2) 54-6 (Eng) the autoxidation of Cu(CH$_3$CN)$_4$BF$_4$ in dimethylsulphoxide is described which gives such a product.

The presence of the Cu-OO-X group in the catalysts may be established by infra-red spectroscopic examination and by the tests listed on page 988 of the article in Inorg. Nucl. Chem. Letters in particular by the liberation of iodine from acidified potassium iodide solution.

Other peroxides may be used in the preparation of the catalyst as alternatives to hydrogen peroxide. Thus the peroxide may be inorganic e.g. barium peroxide or organic e.g. benzoyl peroxide. The reaction may be carried out under conditions similar to those used for hydrogen peroxide, a solvent being chosen to match the reactants.

The olefinic compound which may be used in the process according to the invention may be a hydrocarbon or may contain functional groups provided that these do not interfere with the oxidation reaction. Hydrocarbon olefinic compounds preferably contain up to 20 carbon atoms and may have one or more olefinic bonds which may be internal or terminal. Preferred groups of olefinic compounds for use in the process are $C_2$ to $C_4$ monoolefines, particularly ethylene and propylene and $C_4$ to $C_6$ diolefines particularly butadiene. Olefinic compounds containing non-olefinic substituents which may be used in the process include olefinic acids, alcohols aldehydes, esters and nitriles. In particular, the olefinic compound may be methacrylic acid or acrylic acid or a derivative thereof e.g. an ester with a $C_1$ to $C_6$ alcohol, or may be allyl alcohol, acrolein, methacrolein, acrylonitrile or methacrylonitrile. The olefinic compound may also be a long chain unsaturated fatty acid or derivative thereof e.g. a $C_{10}$ to $C_{20}$ acid such as oleic acid.

The process according to the invention may be carried out in the liquid or vapour phase. When the reactants and products of the process are gaseous under the conditions of the reaction e.g. ethylene and propylene and ethylene oxide and propylene oxide respectively the process may be carried out completely in the vapour phase over the solid catalyst. Alternatively the reactants may be gaseous and the products of the process liquid e.g. when ethylene or propylene are oxidised in the presence of water to ethylene glycol and propylene glycol respectively.

Although the catalyst which is used in the process according to the invention is insoluble it may be convenient to carry out the process, when in the liquid phase, in the presence of a solvent for the reactants and/or products of the process. The solvent may be chosen from a wide range of compounds the basic requirement being that the reactants in particular and preferably the product of the process should dissolve and that the solvent should not interfere with the reaction itself nor should it be extensively changed by the reaction. It is however possible to use as solvent excess of a substance which will react with the olefine oxide formed. In this way, for instance, water may give rise to a glycol product, a phenol or alcohol to an ether and a carboxylic acid to an ester.

Suitable alcohols include aliphatic, cycloaliphatic and araliphatic alcohols. More especially they include alkanols, particularly those having from 1 to 6 carbon atoms, for example methanol, ethanol, n-propanol, isopropanol, butanols, pentanols and hexanols, alkandiols, particularly those having from 1 to 6 carbon atoms, for example ethylene glycol, propane-1,2-diol, propane-1,3-diol, butane-1,4-diol, pentane-diols and hexanediols, alkenepolyols, for example glycerol and trimethylolpropane, aralkanols, for example benzyl alcohol and 2-phenylethanol, and cycloalkanols, for example cyclopentanol, methylcyclopentanols, cyclohexanol and methylcyclohexanols. Particularly suitable alcohols include ethanol and isopropanol.

Suitable phenols include phenol itself, alkylphenols, for example cresols, ethylphenols and xylenols and halogenophenols, especially chlorophenol and di- and tri-chlorophenols. m-Cresol is a particularly suitable phenol.

Suitabe carboxylic acids include aliphatic, cycloaliphatic, araliphatic and aromatic carboxylic acids. More especially they include alkane carboxylic acids, particularly those having from 2 to 6 carbon atoms in the alkane residue, for example acetic acid, propionic acid, butyric acid, isobutyric acid, valeric acid or caproic acid, cycloalkane carboxylic acids, for example cyclohexane carboxylic acid and cyclohexylacetic acid, aralkyl carboxylic acids, for example phenylacetic acid, aryl carboxylic acids, for example benzoic acid, toluic acids and anisic acids, and naphthenic acids. Acetic acid is particularly suitable.

Other useful solvents include nitriles, ketones and amides. Suitable nitriles include aliphatic, and aromatic nitriles. More especially they include alkyl nitriles and alkylene dinitriles, particularly those having from 1 to 6 carbon atoms in the alkyl or alkylene residue, for example acetonitrile, propionitrile, butyronitrile, hexanonitrile, glutarodinitrile, adiponitrile, and succindinitrile, higher polynitriles, cycloalkyl nitriles, for example cyclohexyl cyanide, aralkyl nitriles, for example benzyl cyanide and $\alpha,\alpha'$-xylylene dinitrile and aryl nitriles, for example benzonitrile, tolunitriles, phthalodinitrile and terephthalodinitrile. Particularly suitable nitriles include acetonitrile, propionitrile and adiponitrile.

Suitable ketones include aliphatic, cycloaliphatic, araliphatic aromatic and cyclic ketones. More especially they include dialkyl ketones, particularly those having from 1 to 6 carbon atoms in the alkyl residues, for example acetone, methyl ethyl ketone and methyl isobutyl ketone, diketones, for example acetylacetone, cyclic ketones, for example cyclopentanone, methylcyclopentanone, cyclohexanone and methylcyclohexanone, alkyl aryl ketones, for example acetophenone, and diaryl ketones, for example benzophenone. Acetone and acetylacetone are particularly suitable ketones.

Suitable amides include in particular aliphatic carboxylic amides and their N-substituted derivatives. More especially they include carboxylic amides, particularly those having from 1 to 4 carbon atoms, and their N-alkyl and N,N-dialkyl derivatives especially those having from 1 to 4 carbon atoms in the alkyl residues, for example formamide, N-methylformamide, N,N-dimethylformamide, acetamide, N-N-dimethylacetamide and propionamide. They also include cyclic amides for example N-methyl-2-pyrrolidone. Dimethylformamide is a particularly suitable amide.

Suitable ethers include aliphatic ethers araliphatic ethers, aromatic ethers and cyclic ethers. More especially they include dialkyl ethers, for example di-isopropyl ether and methyl butyl ether, bis-ethers and polyethers for example 1,2-dimethoxyethane, 1,2-dimethoxypropane and diethyleneglycol dimethylether (diglyme), cyclic ethers, for example tetrahydrofuran, tetrahydropyran, dioxan, diphenylene oxide and crown ether (6,7,9,10,17,18,20,21-octahydrodibenzo(b,k)(1,4,7,10,13,16)-hexaoxycyclo-octadiene), alkyl aryl ethers, for example anisole and phenetole, diaralkyl ethers, for example dibenzyl ether, and diaryl ethers for example diphenyl oxide. Dimethoxyethane, diglyme and tetrahydrofuran are particularly suitable ethers.

Suitable solvents also include compounds which contain two or more of the functional groups which characterise, respectively, the said nitriles, alcohols, phenols, ethers, acids, ketones and amides, or contain one or more of the said functional groups in combination with some other group. Such compounds include, for example etheralcohols, for example ethylene glycol monomethyl and monoethyl ether, nitrile-acids, for example cyanoacetic acid and $\alpha$-cyanovaleric acid, halogenoacids, for example chloroacetic acid, dichloroacetic acid and trichloroacetic acid and nitrileesters, for example ethyl cyanoacetate.

Other suitable solvents include esters, especially the esters formed from the alcohols and acids already described as suitable solvents. Particularly suitable esters are the lower alkylesters (e.g. where lower alkyl has from 1 to 4 carbon atoms) of aliphatic mono- or di-carboxylic acids especially those having from 1 to 6 carbon atoms, for example methyl acetate, ethyl acetate, isopropyl acetate, ethyl propionate, methyl butyrate, dimethyl succinate, dimethyl glutarate and diethyl adipate.

Other suitable solvents include hydrocarbons and halogenated hydrocarbons. Such solvents include both aliphatic, cycloaliphatic and aromatic hydrocarbons, and their halogenated derivatives, for example hexane, cyclohexane, benzene, toluene, xylene, chloroform, carbon tetrachloride, trichloroethylene, tetrachloroethane, dibromoethane, chlorobenzene, bromobenzene, dichlorobenzene, trichlorobenzene and diphenyl.

Other suitable solvents include thioethers, that is sulphides, including cyclic sulphides, for example dimethyl sulphide, diethyl sulphide, dipropyl sulphide, dibutyl sulphide, diamyl sulphide, dihexyl sulphide, methyl ethyl sulphide, thiophen, tetrahydrothiophen, pentamethylene sulphide, dicyclohexyl sulphide, dibenzyl sulphide, diphenyl sulphide, ditolyl sulphide and thiodiglycol.

Other suitable solvents include sulphoxides and sulphones, especially dialkyl sulphoxides and sulphones, particularly where the alkyl group has from 1 to 6 carbon atoms, and cyclic sulphoxides and sulphones, for example dimethyl sulphoxide, diethyl sulphoxide, diethyl sulphone, tetramethylene sulphoxide, tetramethylene sulphone, (sulpholane) and pentamethylene sulphoxide and pentamethylene sulphone.

The oxygen may be used as such or in admixture with non-reactive gases such as nitrogen. Air is particularly suitable oxygen-containing gas, but mixtures of oxygen and nitrogen with a higher or lower proportion of oxygen than that of the air may also be used.

In the liquid phase the process of the invention may conveniently be carried out by passing gaseous olefinic compound and oxygen or oxygen-containing gas into a solvent in contact with the catalyst. Alternatively, the olefinic compound may be kept in the liquid phase if necessary under pressure with the catalyst and the solvent and the oxygen or oxygen-containing gas passed through. It is not essential however for the oxygen or oxygen-containing gas to be contacted with the catalyst simultaneously with the olefinic compound. It is possible, for example, to pass the olefinic compound on the one hand and oxygen or oxygen-containing gas on the other hand alternately over the catalyst.

The process is preferably carried out at a temperature in the range 10° to 200° C. The reaction may be carried out at atmospheric pressure but elevated pressures may be used particularly where a gaseous olefinic compound such as ethylene or propylene is a reactant. Pressures in the range 1 to 100 bar are very suitable, 1 to 20 bar being preferred.

The catalyst is used in the process in a catalytic amount based on the amount of olefinic compound to be reacted. For example, the amount of catalyst may be 0.001 mole to 0.2 mole per mole of olefinic compound with which it is in contact.

As an additional feature of the process according to the invention it is preferred to include a source of iodine. The iodine source may be molecular iodine or an iodine-containing compound e.g. an alkali metal iodide such as sodium or potassium iodide, or copper iodide. One method of providing the iodine is to prepare the catalyst from a mixture of cuprous salts one of which is cuprous iodide. The amount of iodine or iodine-containing compound present is preferably in the range 0.01 to 3 wt % based on the weight of catalyst present.

The primary products of the process are olefine oxides but the latter, being highly reactive compounds, may react further e.g. with the reaction solvent as described earlier in this specification or with compounds e.g. water deliberately introduced for this purpose. Certain olefinic compounds particularly diolefines e.g. butadiene may form the dioxide as one product but also the internal condensate, a furan, as another.

The invention is illustrated but not limited by the following Examples in which the catalyst was prepared as follows:

A solution of 90 grams cuprous bromide dissolved in 350 mls propionitrile was added over a period of 4 hours at room temperature to a mixture of 624 mls of a 30% w/v aqueous solution of hydrogen peroxide in 3000 mls water. The mixture was allowed to stand overnight with stirring and the greenish blue precipitate filtered off. The precipitate was then washed with water, acetone, propionitrile and acetone and dried at 70° C. under a pressure of 2 mm Hg. The catalyst was analysed for copper and the presence of the C-OO- bond confirmed by infra-red examination and by the liberation of iodine from an acidified solution of potassium iodide.

% copper found 46.90%
Calculated for

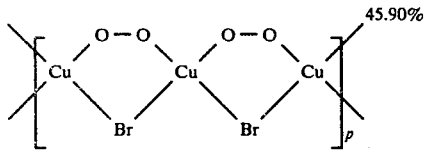
45.90%

EXAMPLE 1 Oxidation of butadiene 1 gram of the catalyst was mixed with the following:

| cuprous iodide | 0.1 gram |
|---|---|
| propionitrile | 10 mls |
| water | 0.2 mls |
| butadiene | 10 mls | and the mixture stirred in a magnetically stirred 250 ml stainless steel autoclave for 24 hours at room temperature under 7 bar pressure of a 50/50 by volume mixture of oxygen and nitrogen.

Analysis of the reaction product by gas-liquid chromatography demonstrated the formation of 0.4 gram of 2-butene-1,4-diol and 0.1 gram 3-butene-1,2-diol.

EXAMPLE 2 Oxidation of Ethylene 2 grams of the catalyst were mixed with,

| cuprous iodide | 0.1 gram |
|---|---|
| propionitrile | 20 mls |
| water | 0.1 ml | and the mixture stirred at room temperature for 24 hours under a pressure of ethylene (3.5 bar) and a 50/50 volume mixture of oxygen and nitrogen (7 bar).

Analysis by gas-liquid chromatography of the gas at 10 bar indicated the presence of 0.072% by volume of ethylene oxide (0.216% conversion of ethylene charged) and of the liquid 0.06 gram of ethylene glycol (2.8% conversion of the ethylene charged).

EXAMPLE 3 Oxidation of Propylene 2 grams of the catalyst were mixed with the following:

| cuprous iodide | 0.1 gram |
|---|---|
| propionitrile | 20 mls |
| water | 0.2 ml | and the mixture stirred at room temperature for 24 hours under a pressure of propylene (3.5 bar) and a 50/50 volume mixture of oxygen and nitrogen (7 bar).

Analysis by gas-liquid chromatography of the gas at 7 bar indicated the presence of 0.05% by volume of propylene oxide (0.1% conversion based in propylene charged).

EXAMPLE 4 Oxidation of Propylene

The catalyst prepared as described above was used in the form of 2 mm diameter pellets 15 grams of which were packed with glass beads in a glass tubular reactor. A gas mixture consisting of 50% by volume propylene and 50% by volume oxygen was passed over the catalyst which was heated to 150° to 180° C. Propylene oxide was detected in the gases leaving the catalyst.

We claim:

1. A process for the oxidation of an olefine to an olefine oxide which comprises reacting an olefine selected from the group consisting of $C_2$ to $C_4$ mono-olefines and butadiene with oxygen in the presence of a copper catalyst which contains copper atoms to each one of which is bonded one or more peroxo groups thereby producing an olefine oxide.

2. A process according to claim 1 in which the catalyst is formed by the reaction of a peroxide with a cuprous compound or with a cupric compound readily convertible to the cuprous form.

3. A process according to claim 1 in which the catalyst is formed by the reaction of a peroxide with cupric acetate, cuprous chloride, cuprous bromide, cuprous iodide or cuprous cyanide.

4. A process according to claim 1 in which the peroxide is hydrogen peroxide.

5. A process according to claim 1 which is conducted in the liquid phase in the presence of a solvent.

6. A process according to claim 1 in which the temperature is in the range 10° to 200° C. and the pressure 1 to 100 bar.

7. A process according to claim 1 in which a source of iodine is present.

8. A process according to claim 1 in which the olefinic compound is ethylene, propylene or butadiene.

9. A process according to claim 1 in which water is present and the olefine oxide is converted to the corresponding glycol.

* * * * *